US011077031B2

(12) United States Patent
Cho et al.

(10) Patent No.: US 11,077,031 B2
(45) Date of Patent: Aug. 3, 2021

(54) OIL-IN-WATER EMULSION COMPOSITION

(71) Applicant: AMOREPACIFIC CORPORATION, Seoul (KR)

(72) Inventors: Young Uk Cho, Yongin-si (KR); Byung Geun Chae, Yongin-si (KR); Sungil Park, Yongin-si (KR); Seong A Cho, Yongin-si (KR); Do Hoon Kim, Yongin-si (KR); Seung Han Park, Yongin-si (KR); Jae il Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 49 days.

(21) Appl. No.: 15/760,575

(22) PCT Filed: Sep. 28, 2016

(86) PCT No.: PCT/KR2016/010830
§ 371 (c)(1),
(2) Date: Mar. 15, 2018

(87) PCT Pub. No.: WO2017/057893
PCT Pub. Date: Apr. 6, 2017

(65) Prior Publication Data
US 2018/0243180 A1     Aug. 30, 2018

(30) Foreign Application Priority Data

Sep. 30, 2015  (KR) .................. 10-2015-0137373

(51) Int. Cl.
| | |
|---|---|
| *A61K 8/06* | (2006.01) |
| *A61Q 19/00* | (2006.01) |
| *A61K 8/37* | (2006.01) |
| *A61K 8/60* | (2006.01) |
| *A61K 8/92* | (2006.01) |
| *A61K 8/362* | (2006.01) |
| *A61K 8/31* | (2006.01) |
| *A61K 8/44* | (2006.01) |

(52) U.S. Cl.
CPC .............. *A61K 8/062* (2013.01); *A61K 8/31* (2013.01); *A61K 8/362* (2013.01); *A61K 8/375* (2013.01); *A61K 8/442* (2013.01); *A61K 8/60* (2013.01); *A61K 8/602* (2013.01); *A61K 8/922* (2013.01); *A61Q 19/00* (2013.01); *A61K 2800/10* (2013.01); *A61K 2800/21* (2013.01); *A61K 2800/592* (2013.01); *A61K 2800/596* (2013.01); *A61Q 19/007* (2013.01)

(58) Field of Classification Search
None
See application file for complete search history.

(56) References Cited

U.S. PATENT DOCUMENTS

| | | | | |
|---|---|---|---|---|
| 4,671,957 | A * | 6/1987 | Holtshousen | A61K 9/0014 424/667 |
| 5,221,707 | A * | 6/1993 | Chihara | C08G 18/10 524/267 |
| 6,919,076 | B1 * | 7/2005 | Green | A61K 8/0208 424/94.5 |
| 2003/0012759 | A1 * | 1/2003 | Bowen-Leaver | A61K 8/042 424/70.12 |
| 2003/0114324 | A1 * | 6/2003 | Lange | A61K 8/0208 510/130 |
| 2003/0133900 | A1 * | 7/2003 | McLaughlin | A61K 8/345 424/70.22 |
| 2004/0120974 | A1 * | 6/2004 | Gesslein | A61K 8/37 424/401 |
| 2004/0228813 | A1 * | 11/2004 | Candau | A61Q 17/04 424/59 |
| 2005/0196363 | A1 * | 9/2005 | Horino | A61K 8/11 424/59 |
| 2007/0128146 | A1 * | 6/2007 | Fujino | A61K 8/062 424/70.31 |
| 2007/0154500 | A1 * | 7/2007 | Cassin | A61K 8/585 424/401 |
| 2007/0265209 | A1 * | 11/2007 | Goget | A61K 8/06 514/23 |
| 2007/0280979 | A1 * | 12/2007 | Shinohara | A61K 8/06 424/401 |
| 2008/0206290 | A1 * | 8/2008 | Schulz | A61K 8/0208 424/401 |
| 2008/0223535 | A1 * | 9/2008 | Eichhorn | D21H 21/22 162/123 |

(Continued)

FOREIGN PATENT DOCUMENTS

| | | |
|---|---|---|
| FR | 2902654 A1 * | 12/2007 |
| JP | 2007145721 A | 6/2007 |

(Continued)

OTHER PUBLICATIONS

Rybinski et al. "Alkyl Polyglycosides" in Novel Surfactants: Preparation, Applications, and Biodegradability. Holmberg ed. Marcel Dekker Inc.: New York 2003 p. 35 and 38-40 (Year: 2003).*

(Continued)

*Primary Examiner* — Robert A Wax
*Assistant Examiner* — Caralynne E Helm
(74) *Attorney, Agent, or Firm* — McCoy Russell LLP

(57) ABSTRACT

The present invention relates to: an oil-in-water emulsion composition having a viscosity of 1,500-50,000 cps, and comprising an anionic surfactant and a sugar surfactant so as to satisfy the following relational expression 1; and a cosmetic composition containing the same. [Relational expression 1] $0.01 \leq A/B \leq 1$ (In relational expression 1, A is the wt % of the anionic surfactant, and B is the wt % of the sugar surfactant, wherein the wt % of each ingredient is based on the total weight of the composition, and B is 1-30 wt %.)

7 Claims, 3 Drawing Sheets

(56) References Cited

U.S. PATENT DOCUMENTS

| | | | | |
|---|---|---|---|---|
| 2008/0241202 A1* | 10/2008 | de Souza Costa | | A61K 8/06 424/401 |
| 2009/0104294 A1* | 4/2009 | Wenk | | A61K 8/97 424/756 |
| 2010/0021399 A1* | 1/2010 | Rampoldi | | A61K 8/06 424/59 |
| 2010/0028275 A1* | 2/2010 | Ansmann | | A61K 8/06 424/59 |
| 2010/0098765 A1* | 4/2010 | Mercado | | A61Q 19/00 424/489 |
| 2010/0278770 A1* | 11/2010 | Arditty | | A61K 8/06 424/70.7 |
| 2011/0244030 A1* | 10/2011 | Lebel | | A61K 9/12 424/450 |
| 2012/0136067 A1* | 5/2012 | Ruppert | | A61K 8/06 514/685 |
| 2012/0289597 A1* | 11/2012 | Farber | | A61K 9/0014 514/551 |
| 2014/0086968 A1* | 3/2014 | Grascha | | A61K 9/0014 424/405 |
| 2014/0294965 A1* | 10/2014 | Brown | | A61K 8/0241 424/489 |
| 2016/0051611 A1* | 2/2016 | Banov | | A61K 36/58 424/769 |

FOREIGN PATENT DOCUMENTS

| | | | |
|---|---|---|---|
| KR | 20090056028 A | 6/2009 | |
| KR | 20110036259 A | 4/2011 | |
| KR | 20110055051 A | 5/2011 | |
| KR | 101044196 B1 | 6/2011 | |
| KR | 20140047443 A | 4/2014 | |
| WO | WO-2014060400 A2 * | 4/2014 | A45D 7/02 |

OTHER PUBLICATIONS

Cosmetic Ingredient Review Safety Assessment of Glycerin as Used in Cosmetics 2014 pp. 1-19 (Year: 2014).*

Yeh et al. Water Science & Technology 2005 52(1-2):343-349 (Year: 2005).*

ISA Korean Intellectual Property Office, International Search Report Issued in Application No. PCT/KR2016/010830, dated Dec. 29, 2016, WIPO, 4 pages.

* cited by examiner

[FIG. 1]
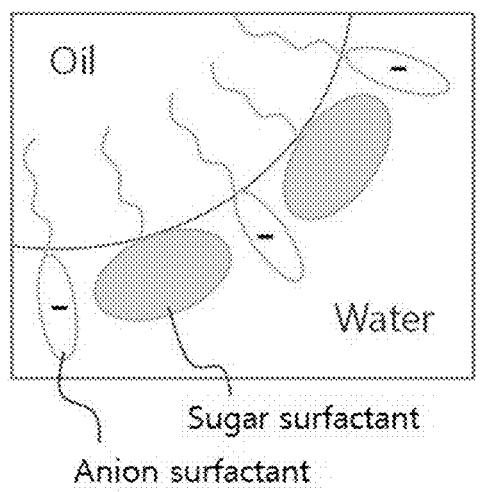

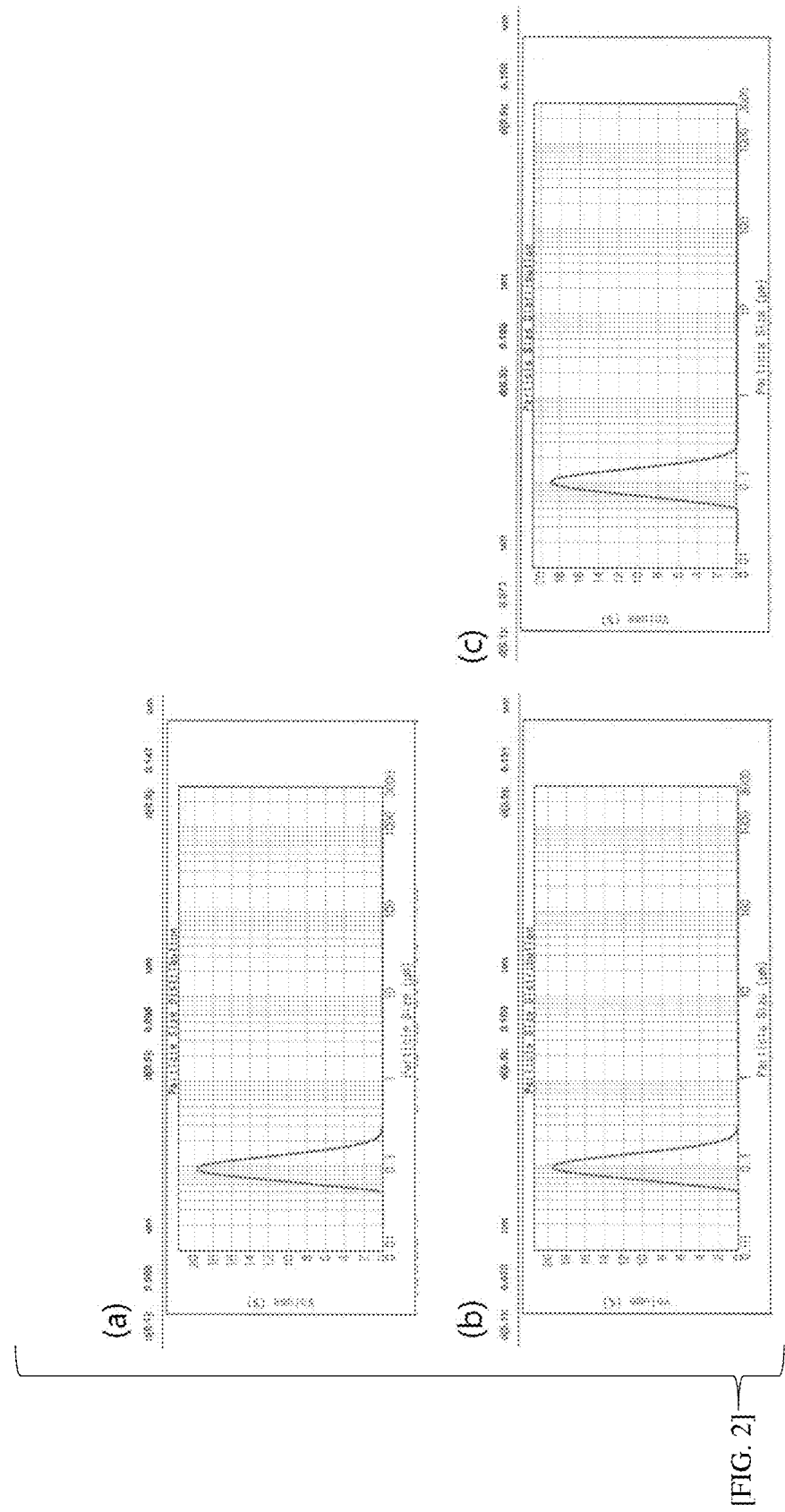
[FIG. 2]

[FIG. 3]
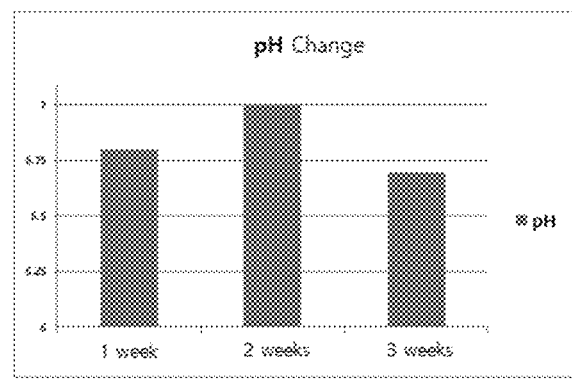

OIL-IN-WATER EMULSION COMPOSITION

CROSS-REFERENCE TO RELATED APPLICATIONS

The present application is a U.S. National Phase of International Patent Application Serial No. PCT/KR2016/010830 entitled "OIL-IN-WATER EMULSION COMPOSITION," filed on Sep. 28, 2016. International Patent Application Serial No. PCT/KR2016/010830 claims priority to Korean Patent Application No. 10-2015-0137373, filed on Sep. 30, 2015. The entire contents of each of the above-cited applications are hereby incorporated by reference in their entirety for all purposes.

TECHNICAL FIELD

The present invention relates to an oil-in-water emulsion composition.

BACKGROUND ART

An emulsion is a mixture in which oil droplets are dispersed in water (oil-in-water type), or water droplets are dispersed in oil (water-in-oil type), and this emulsion is thermodynamically very unstable, and has a nature of being eventually phase-separated by various routes such as flocculation, sedimentation, creaming, particle growth (Ostwald ripening) and coalescence.

Meanwhile, a solid emollient has been used for high moisturizing ability and an improved feeling of use of cosmetics, however, oil and fats have a strong tendency to agglomerate together by the action of strong attraction by the physical characteristics thereof, and when a high content of emollient is contained, the stability of the emulsion is easily broken so that phase separation into an oil phase and an aqueous phase occurs.

Thus, the present inventors made an effort to improve the conventional problems, and as a result, even with a high content of solid emollient, the stability of an oil-in-water emulsion composition may be secured by using two kinds of surfactants.

As such, as the related document for stability improvement of the oil-in-water emulsion composition, Korean Patent Registration Publication No. 10-1044196 has been suggested.

DISCLOSURE

Technical Problem

An object of the present invention is to provide an oil-in-water emulsion composition stably containing a high content of solid emollient, and a cosmetic composition including the same.

Technical Solution

In one general aspect, an oil-in-water emulsion composition having a viscosity of 1,500-50,000 cps includes an anionic surfactant and a sugar surfactant so as to satisfy the following Equation 1:

$$0.01 \leq A/B \leq 1 \quad \text{[Equation 1]}$$

wherein A is a wt % of the anionic surfactant, and B is a wt % of the sugar surfactant; and the wt % of each component is based on a total weight of the composition, and B is 1-30 wt %.

In another general aspect, a cosmetic composition includes the oil-in-water emulsion composition.

Advantageous Effects

The oil-in-water emulsion composition according to the present invention may form a very stable emulsion system by using two kinds of surfactants which are an anionic surfactant and a sugar surfactant. Further, accordingly, even with the use of a high content of solid emollient, phase separation does not occur very often, even after a long time has elapsed.

DESCRIPTION OF DRAWINGS

FIG. 1 is a drawing schematically illustrating a structure of an oil-in-water emulsion composition according to an exemplary embodiment of the present invention.

FIG. 2 is particle size distribution charts obtained by measuring an emulsified particle size in an oil-in-water emulsion composition according to an exemplary embodiment of the present invention over time.

FIG. 3 is a graph obtained by measuring pH of an oil-in-water emulsion composition according to an exemplary embodiment of the present invention over time.

BEST MODE

Hereinafter, the oil-in-water emulsion composition of the present invention will be described in detail with reference to the accompanying drawings. The drawings to be provided below are provided by way of example so that the idea of the present invention can be sufficiently delivered to a person skilled in the art to which the present invention pertains. Therefore, the present invention is not limited to the drawings provided below but may be modified in many different forms. In addition, the drawings suggested below will be exaggerated in order to clear the spirit and scope of the present invention. In addition, like reference numerals denote like elements throughout the specification.

Technical terms and scientific terms used herein have the general meaning understood by those skilled in the art to which the present invention pertains unless otherwise defined, and a description for the known function and configuration obscuring the present invention will be omitted in the following description and the accompanying drawings.

The present invention relates to an oil-in-water emulsion composition having a viscosity of 1,500-50,000 cps, including an anionic surfactant and a sugar surfactant so as to satisfy the following Equation 1:

$$0.01 \leq A/B \leq 1 \quad \text{[Equation 2]}$$

wherein A is a wt % of the anionic surfactant, and B is a wt % of the sugar surfactant; and the wt % of each component is based on a total weight of the composition, and B is 1-30 wt %.

As illustrated in FIG. 1, in the oil-in-water emulsion composition according to the present invention, the surface of emulsified particles has negative zeta potential by the anionic surfactant, thereby generating repulsive force between emulsified particles so as to prevent confluence of emulsified particles, and thus, a thermodynamically stabilized oil-in-water emulsion composition may be obtained. However, when using only the anionic surfactant, the particle size is large by the nature of the emulsified particles, but the anionic surfactant has a low packing parameter of about ⅓ or less, and thus, the curvature of the emulsified particle interfacial layer may not be stably formed. Thus, the present inventors used a sugar surfactant together with the anionic surfactant, so that the sugar surfactant particles are positioned between the anionic surfactant particles disposed in the interfacial layer of the emulsified particles to have a high packing parameter of ⅓ to less than 1, and thus, a stable curvature may be formed to further improve the stability of the emulsion composition.

As such, in order to obtain a stabilized oil-in-water emulsion composition, it is preferred to properly adjust a ratio of the anionic surfactant and the sugar surfactant. As an example, the ratio of the anionic surfactant and the sugar surfactant may satisfy the following Equation 1, as mentioned above, and in Equation 1, A is a wt % of the anionic surfactant, and B is a wt % of the sugar surfactant.

$$0.01 \leq A/B \leq 1 \qquad \text{[equation 3]}$$

That is, the anionic surfactant and the sugar surfactant may have a weight ratio of 1:100-1. When the amount of the anionic surfactant is unduly larger than the amount of the sugar surfactant, the anionic surfactant mainly exists in the interfacial layer of the emulsified particles, and thus, as described above, has a low packing parameter of about ⅓ or less, so that the curvature of the emulsified particle interfacial layer may not be stably formed. As the emulsified particle interfacial layer does not have a stable curvature, the emulsified particles coalesce together or grow, thereby reducing the entire stability of the emulsion composition. On the contrary, when the amount of the sugar surfactant is unduly larger than the anionic surfactant, negative zeta potential is not sufficiently formed on the surface of the emulsified particle, thereby not generating repulsive force between the emulsified particles, and thus, there is a possibility of phase separation within a short time. The weight ratio of the anionic surfactant and the sugar surfactant may satisfy preferably $0.02 \leq A/B \leq 0.5$, more preferably $0.05 \leq A/B \leq 0.2$. Within the above range, sufficient repulsive force between the emulsified particles occurs by the anionic surfactant to form a stable dispersed phase, and the sugar surfactant particles are positioned between the anionic surfactant particles in the same emulsified particles, thereby having a high packing parameter of ⅓ to less than 1, and thus, a stable curvature may be formed to greatly improve the stability of the oil-in-water emulsion composition.

More specifically, the contents of the anionic surfactant and the sugar surfactant may be adjusted depending on the use of the emulsion composition, and specifically for example, the content of the anionic surfactant may be 0.01-3 wt %, and the content of the sugar surfactant may be 1-30 wt %, based on the total weight of the composition. More preferably, the content of the anionic surfactant may be 0.1-1 wt %, and the content of the sugar surfactant may be 3-10 wt %, based on the total weight of the composition. Within the above range, sufficient repulsive force between the emulsified particles occurs, so that the surface of the emulsified particles may have proper negative zeta potential to form a stable dispersed phase, and as the sugar surfactant particles are positioned between the anionic surfactant particles in the same emulsified particles, it may have a high packing parameter of ⅓ to less than 1, resulting in forming a stable curvature, thereby obtaining an oil-in-water emulsion composition having greatly improved stability. As an example, the surface of the emulsified particles by the anionic surfactant may have negative zeta potential of −160 to −50, resulting in sufficiently generating repulsive force between the emulsified particles to form a stable dispersed phase.

As the hydrophilic group of the anionic surfactant is positioned on the surface of the emulsified particle, and the lipophilic group of the anionic surfactant is positioned inside of the emulsified particle, the size of the emulsified particles may be adjusted by the size of the hydrophilic group and the lipophilic group. That is, in order to form the emulsified particles having a small particle diameter, it is preferred that the size of the hydrophilic group and/or the lipophilic group is small, however, in the case that the lipophilic group is unduly short, skin irritation may be strong, and thus, it is preferred to use a compound having a length of at least the certain number of carbon atoms. Specifically, the anionic surfactant according to an exemplary embodiment of the present invention may be a carboxylic acid-based surfactant, an amino acid-based surfactant, or a mixture thereof. Since the hydrophilic group of the anionic surfactant as such has a smaller size than that of a sulfate-based surfactant or a phosphate-based surfactant, the anionic surfactant may be preferred for forming the emulsified particles having a smaller size. Besides, the anionic surfactant according to an exemplary embodiment may contain a C16 or higher aliphatic alkyl group, aliphatic alkylether group, aliphatic alkylester group, or aliphatic alkylacyl group, more preferably a C16-C22 aliphatic alkyl group, aliphatic alkylether group, aliphatic alkylester group, or aliphatic alkylacyl group. The lipophilic group as such may be linear or branched, saturated or unsaturated hydrocarbon. When the carbon number is less than 16, skin irritation is stronger, and thus, it may not be preferred for using the cosmetic composition, in particular skin, lotion, cream or the like by applying it on the skin. As a non-limited specific example, the anionic surfactant may be sodium stearate, sodium stearoyl lactylate, sodium palmitoyl sarcosinate, monosodium palmitoyl glutamate, disodium palmitoyl glutamate, sodium stearoyl sarcocinate, monosodium stearoyl glutamate, disodium stearoyl glutamate, or the like, but not limited thereto, and herein, a potassium salt, an ammonium salt or the like may be used instead of the sodium salt.

As such, by using the anionic surfactant, negative zeta potential is formed on the surface of the emulsified particles, and by adjusting the size of the anionic surfactant, the size of the emulsified particles may be adjusted to be smaller. When the small-sized emulsified particles are used as the cosmetic composition and the like, the effective component may be effectively transferred to the skin, emulsion stability is improved, and as described below, when an emollient is added, degeneration of an oily emollient may be prevented. As an example, the average diameter of the emulsified particles in the oil-in-water emulsion composition according to an exemplary embodiment of the present invention may be 10-300 nm, but not limited thereto.

The sugar surfactant may be used without particular limitation, as long as it is commonly used in the art, and for example, a monosaccharide surfactant, a disaccharide surfactant, or a mixture thereof may be used. Specifically, the sugar surfactant may be a compound of a C12 or higher aliphatic alkyl group, aliphatic alkylether group, aliphatic alkylester group, or aliphatic alkylacyl group bonded to monosaccharide or disaccharide. More specifically, the monosaccharide surfactant may be a compound containing xylulose, ribose, arabinose, xylose, fructose, allose, glucose, mannose or galactose, and the disaccharide surfactant may be a compound containing sucrose, lactose, maltose or trehalose. As a non-limited specific example, polyglyceryl-3 methylglucose distearate, sucrose distearate, ethyl glucose stearate, sucrose monopalmitate or the like may be listed, but not limited thereto.

The oil-in-water emulsion composition according to an exemplary embodiment of the present invention may have a viscosity of 1,500-50,000 cps, as described above. A conventional emulsion composition has higher viscosity by adding a thickening agent and the like, but since the thickening agent causes aggregation, skin stickiness, reduced feeling of use, and the like, it is preferred not to use the thickening agent. However, the present invention uses the anionic surfactant, the sugar surfactant, and a specific kind of solid emollient, and is subjected to a high-pressure emulsification process, thereby forming high viscosity without the thickening agent, as described below. The viscosity may be preferably 5,000-30,000 cps, more preferably 8,000-20,000 cps.

In addition, the oil-in-water emulsion composition according to an exemplary embodiment of the present invention may further include 5-30 wt % of a solid emollient, based on the total weight of the composition, and the solid emollient may be included at 5-25 wt %, more preferably 10-20 wt %, based on the total weight of the composition. The solid emollient is used for skin moisturizing, elasticity and the like, as described above, and within the above range, the effect of skin moisturizing and elasticity enhancement may be excellent, and feeling of use may be outstanding due to smoothness without stickiness. However, since the solid emollient has a strong nature of being aggregated with each other, and has a high possibility of being phase-separated after a long time, adding a high content of solid emollient has a problem in greatly reducing stability of the emulsion composition. Thus, as described above, the present inventors used the anionic surfactant and the sugar surfactant in combination, thereby greatly improving the stability of the emulsion composition, and thus, even with the use of a high content of the solid emollient, an oil-in-water emulsion composition having high stability even after a long time was obtained.

As such, in order to obtain an oil-in-water emulsion composition having excellent stability even in the case of using a high content of a solid emollient, it is more preferred to use a specific solid emollient. Specifically, the solid emollient may be a butter emollient having 60 wt % or more of lauric acid and myristic acid in the emollient. Generally, since shear butter, sal butter, kukum butter and the like which are much used as the solid emollient have a high content of aliphatic acid (stearic acid, oleic acid or the like) having more carbon atoms than lauric acid and myristic acid, and when preparing the oil-in-water emulsion composition, an emulsion composition having a high viscosity (preferably 1,500-50,000 cps) is not formed, the tendency of the emulsified particles to aggregate is stronger so that the size of the emulsified particles may be larger, and the dispersion uniformity of the emollient particles is reduced so that the appearance of the emulsion composition may be unclear. Further, as the butter emollient containing the aliphatic acid having less carbon atoms than stearic acid, oleic acid or the like, such as lauric acid and myristic acid is used, the skin absorption rate of the emollient may be high, and as the emollient has a low melting point, it may have excellent spreadability. As a non-limited specific example, the butter emollient may be any one or two or more selected from the group consisting of Murumuru butter, Tucuma butter, Ucuuba butter and the like. The Murumuru butter may contain 44-52 wt % of lauric acid and 22-28 wt % of myristic acid, the Tucuma butter may contain 44-55 wt % of lauric acid and 22-30 wt % of myristic acid, and the Ucuuba butter may contain 16-20 wt % of lauric acid and 72-76 wt % of myristic acid.

Further, in one aspect, the present invention also relates to a cosmetic composition including the oil-in-water emulsion composition as described above. The formulation of the cosmetic composition is not particularly limited, however, for being used on the skin, in the mucous membrane, scalp, hair or the like, the cosmetic composition may be formulated into for example, basic cosmetics such as softening tonic, nutrition tonic, lotion, cream, pack, gel, patch or spray (mist); color cosmetics such as lipsticks, makeup base or foundation; cleansers such as shampoo, conditioners, body cleansers, toothpaste or oral cleansers; hair fixatives such as hair tonic, gel or mousse; and a cosmetic composition for hair such as bleaching agents or hair dyes. Further, the oil-in-water emulsion composition of the present invention may be medicines, quasi-drugs and the like such as lotion, ointment, gel, cream, patch or sprays.

Further, in another aspect, the present invention also relates to a preparation method of the oil-in-water emulsion composition as described above.

Specifically, the preparation method of the oil-in-water emulsion composition according to the present invention may include a) preparing a mixture including an anionic surfactant, a sugar surfactant and a solid emollient; and b) subjecting the mixture to high-pressure emulsification to prepare an emulsion composition.

In step a) according to an exemplary embodiment, since the anionic surfactant, the sugar surfactant and the solid emollient may be prepared as described above for the oil-in-water emulsion composition, the detailed description thereof will be omitted. In addition, the mixture may, of course, further include aqueous components such as purified water and alcohol; oily components such as oil and wax; colorants such as dyes and pigments; and additives such as fragrances, moisturizers, preservatives, whitening agents, sunscreen agents, anti-wrinkle agents, vitamins, plant extracts and/or animal extracts, which are commonly used in the art.

Next, when the mixture is prepared, the oil-in-water emulsion composition may be prepared by a high-pressure emulsification process. Typically, the emulsion composition after being subjected to high-pressure emulsification tends to have lower viscosity than the viscosity of the mixture before being subjected to high-pressure emulsification, however, in the present invention, the prepared emulsion composition has higher viscosity after being subjected to high-pressure emulsification, and thus, high viscosity may be formed without using the thickening agent which causes aggregation, skin stickiness, reduced feeling of use, and the like. Specifically, the viscosity according to an exemplary embodiment of the present invention may be 1,500-50,000 cps, preferably 5,000-30,000 cps, more preferably 8,000-20,000 cps.

Specifically, in step b) according to an exemplary embodiment, the high-pressure emulsification treatment may be carried out using a high-pressure emulsifier, and more specifically, the mixture prepared in step a) is added to the high-pressure emulsifier, and high-pressure emulsification with a pressure of 500 bar or more is repeatedly performed three times or more, thereby preparing the oil-in-water emulsion composition. More preferably, the high-pressure emulsification may be repeatedly performed with a pressure of 800-1,200 bar three to eight times. By doing so, even in the case of using a high content of the emollient is used, the stability of the emulsion composition may be secured, and the emulsion composition having high viscosity and transparency may be prepared. In addition, the oil-in-water emulsion composition having an average diameter of the emulsified particles in the composition of 10-300 nm, more preferably 50-200 nm may be prepared.

Hereinafter, the oil-in-water emulsion composition according to an exemplary embodiment of the present invention will be described in more detail by the following Examples. However, the following Examples are only a reference for describing the present invention in detail, and the present invention is not limited thereto, and may be implemented in various forms. Further, unless otherwise stated, the unit of added materials herein may be wt %.

Example 1

Each component described in the following Table 1 was mixed, and repeatedly subjected to high-pressure emulsification with a pressure of 800-1,500 bar 3 to 8 times, thereby obtaining an oil-in-water emulsion composition having a viscosity of 15,000 cps. (Viscosity before high-pressure emulsification: 300-400 cps)

TABLE 1

| Components | Content (wt %) |
|---|---|
| Sodium stearoyl glutamate | 0.5 |
| Polyglyceryl-3 methylglucose distearate | 5 |
| Squalane | 10 |
| Murumuru butter | 10 |
| Glycerin | 10 |
| Ethanol | 5 |
| Purified water | 59.5 |

[Experimental Example 1] Measurement of Emulsified Particle Size

The emulsified particle size (diameter) change of the oil-in-water emulsion composition prepared in Example 1 was measured, and the stability of the formulation was evaluated.

FIG. 2 is data of measurement of the particle size distribution of the emulsified particles (a) after 1 week of preparation, (b) after 2 weeks of preparation, and (c) after 4 weeks of preparation, which is summarized in Table 2. As shown in FIG. 2 and Table 2, it is confirmed that there was little change in the emulsified particle size between immediately after preparation and 4 weeks after preparation, and thus, the oil-in-water emulsion composition according to an exemplary embodiment of the present invention has very high stability.

TABLE 2

| | Immediately after preparation | After 1 week | After 2 weeks | After 4 weeks |
|---|---|---|---|---|
| d(0.1), μm | 0.070 | 0.069 | 0.070 | 0.073 |
| d(0.5), μm | 0.099 | 0.098 | 0.100 | 0.106 |
| d(0.9), μm | 0.146 | 0.147 | 0.151 | 0.160 |

[Experimental Example 2] Measurement of pH Change

The pH change of the oil-in-water emulsion composition prepared in Example 1 was measured, and the stability of the formulation was evaluated.

The pH change degree was measured from immediately after preparation to 3 weeks after preparation, and as shown in FIG. 3 and Table 3, it is confirmed that there was little change in pH, and thus, the oil-in-water emulsion composition according to an exemplary embodiment of the present invention has very high stability.

TABLE 3

| | Immediately after preparation | After 1 week | After 2 weeks | After 3 weeks |
|---|---|---|---|---|
| pH | pH 6.9 | pH 6.8 | pH 7 | pH 6.7 |

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. An oil-in-water emulsion composition consisting of an anionic surfactant and a sugar surfactant so as to satisfy the following Equation 1, and 10-30 wt % of at least one solid emollient selected from the group consisting of murumuru butter, tucuma butter, and ucuuba butter, purified water, and optionally at least one additive selected from the group consisting of alcohol, oil, wax, a dye, a pigment, a fragrance, a moisturizer, a preservative, a whitening agent, a sunscreen agent, an anti-wrinkle agent, a vitamin, a plant extract, and an animal extract:

$$0.01 \leq A/B \leq 1 \qquad \text{Equation 1}$$

wherein A is a wt % of the anionic surfactant, and B is a wt % of the sugar surfactant; and the wt % of each component is based on a total weight of the composition, and B is 3-30 wt %, wherein the sugar surfactant is polyglyceryl-3 methylglucose distearate or sucrose monopalmitate, wherein the anionic surfactant is sodium stearate, sodium stearoyl lactylate, sodium palmitoyl sarcosinate, monosodium palmitoyl glutamate, disodium palmitoyl glutamate, sodium stearoyl sarcosinate, monosodium stearoyl glutamate or disodium stearoyl glutamate, and wherein an average diameter of emulsified particles is 10-300 nm.

2. The oil-in-water emulsion composition of claim 1, wherein the anionic surfactant is included at 0.01-3 wt %, based on the total weight of the composition.

3. The oil-in-water emulsion composition of claim 1, wherein a surface of emulsified particles in the composition has negative zeta potential of −160 to −50.

4. The oil-in-water emulsion composition of claim 1, wherein the sugar surfactant particles are positioned between the anionic surfactant particles disposed in an interfacial layer of emulsified particles to have a packing parameter of ⅓ to less than 1.

5. The oil-in-water emulsion composition of claim 1, wherein the sugar surfactant is polyglyceryl-3 methylglucose distearate, the anionic surfactant is monosodium stearoyl glutamate or disodium stearoyl glutamate, and the solid emollient is Murumuru butter.

6. The oil-in-water emulsion composition of claim 1, wherein the additive is at least one selected from the group consisting of alcohol, a moisturizer and a plant extract.

7. The oil-in-water emulsion composition of claim 6, wherein the sugar surfactant is polyglyceryl-3 methylglucose distearate, the anionic surfactant is monosodium stearoyl glutamate or disodium stearoyl glutamate, and the solid emollient is Murumuru butter.

* * * * *